US012758472B2

(12) United States Patent
Kleczkowski et al.

(10) Patent No.: US 12,758,472 B2
(45) Date of Patent: Oct. 13, 2026

(54) FORMULATION FOR TREATMENT OF MELASMA, HYPERPIGMENTATION, AND DARK SPOTS

(71) Applicants: Julia Kleczkowski, Kinnelon, NJ (US); Ginger King, Parsippany, NJ (US)

(72) Inventors: Julia Kleczkowski, Kinnelon, NJ (US); Ginger King, Parsippany, NJ (US)

( * ) Notice: Subject to any disclaimer, the term of this patent is extended or adjusted under 35 U.S.C. 154(b) by 232 days.

(21) Appl. No.: 18/445,907

(22) Filed: Mar. 19, 2024

(65) Prior Publication Data

US 2025/0295562 A1 Sep. 25, 2025

(51) Int. Cl.
*A61K 8/02* (2006.01)
*A61Q 19/02* (2006.01)

(52) U.S. Cl.
CPC ............ *A61K 8/0204* (2013.01); *A61Q 19/02* (2013.01); *A61K 2800/524* (2013.01)

(58) Field of Classification Search
CPC ............ A61K 8/0204; A61K 2800/524; A61K 8/347; A61K 8/37; A61K 8/375; A61K 8/64; A61K 8/676; A61K 8/922; A61K 8/9789; A61Q 19/02
See application file for complete search history.

(56) References Cited

U.S. PATENT DOCUMENTS

2021/0330568 A1* 10/2021 Carle ........................ A61K 8/64

* cited by examiner

*Primary Examiner* — Robert A Wax
*Assistant Examiner* — Quanglong N Truong
(74) *Attorney, Agent, or Firm* — Dan Delarosa

(57) ABSTRACT

A formulation for treatment of hyperpigmentation and melasma, is provided, comprising five actives consists of: a blend of caprylic or capric triglycerides, hexylresorcinol, and ethyl linoleate; hexylresorcinol; a blend of tetrapeptide and glycerin; a blend of *Rumex occidentalis* extract, ascorbic acid and glycerin; and a blend of *Humulus lupulus* extract, caprylic or capric triglycerides.

10 Claims, No Drawings

FORMULATION FOR TREATMENT OF MELASMA, HYPERPIGMENTATION, AND DARK SPOTS

BACKGROUND OF THE INVENTION

Melasma (also known as Chloasma) is a common skin problem caused by brown to gray-brown patches on the face. Most people get it on their cheeks, chin, nose bridge, forehead, and above the upper lip. Persons of any race can be affected. Melasma is more common in darker skin types than in lighter skin types, and it is particularly more common in light brown skin types. It is more common in women than men. Women are affected nine times more than men. Melasma is rare before puberty and more common in reproductive years. Pregnancy is a common cause of melasma or "mask of pregnancy". Melasma is present in 15% to 50% of pregnant patients. The prevalence varies between 1.5% and 33% depending on the population. It also affects women taking oral contraceptives and hormones.

Etiologic factors include genetic influences, ultraviolet (UV) radiation, pregnancy, hormonal therapies, cosmetics, phototoxic drugs, and antiseizure medications. Melasma stimulates melanocytes by the female sex hormones estrogen and progesterone, producing more melanin pigments when the skin is exposed to the sun.

Genetic predisposition may be a major factor in the development of melasma. Persons with light-brown skin types from regions of the world with high sun exposure are more prone to the development of melasma. Approximately 50% report a positive family history of the condition. Identical twins have been reported to develop melasma.

UV radiation can cause lipids peroxidation in cellular membranes, resulting in free radicals which could stimulate melanocytes to produce excess melanin. Sunscreens that block UV-B radiation (290-320 nm) do not block the longer wavelengths of UV-A and visible radiation (320-700 nm) which also stimulate melanocytes to produce melanin.

Hormones may play a role in developing melasma in some individuals. The mask of pregnancy is known to occur in obstetric patients. The exact mechanism is unknown. Estrogen, progesterone, and melanocyte-stimulating hormone levels are normally increased during the third trimester of pregnancy and may be a factor. Patients with melasma who are nulliparous have no increased levels of estrogen or MSH but show elevated levels of estrogen receptors within the lesions. In addition, melasma with estrogen- and progesterone-containing oral contraceptive pills and diethylstilbestrol treatment for prostate cancer have been observed. A woman who is postmenopausal and given progesterone may develop melasma, while those who are given estrogen alone do not; this implicates progesterone as playing a primary role in the development of melasma.

There is a four-fold increase in thyroid disease in melasma patients. There is an association between the development of melasma and the presence of melanocytic nevi and lentiginous nevi. This would indicate a relationship between the development of melasma and the presence of pigmentation.

All melasma is hyperpigmentation, but not all hyperpigmentation is melasma. Hyperpigmentation is a generalized term to describe any form of discoloration of the skin darker than the natural skin tone. There are various forms of hyperpigmentation, including sun spots, age spots, acne scars, melasma, and post-inflammatory hyperpigmentation. Hyperpigmentation is caused by an increase in melanin in the skin. Melasma presents as dark patches of skin, often symmetrically on the face, that are triggered by various factors like hormonal changes, sun exposure, medications, and genetics.

It can be difficult to differentiate melasma and hyperpigmentation because they present similarly, and an overproduction of melanin causes both. A clue that can help distinguish between melasma and hyperpigmentation is if you have a history of hormonal changes, pregnancy, oral contraceptives, or hormone replacement therapies, which may suggest the discoloration may be melasma. Hyperpigmentation may be sun damage and sun spots if you have a history of chronic sun exposure and tanning. Melasma often presents as broad patches of discoloration, whereas sun spots and other forms of hyperpigmentation may look like small circles or focused dots.

SUMMARY OF THE INVENTION

The formulation of the present invention can treat hyperpigmentation including sun spots, age spots, acne scars, melasma, and post-inflammatory hyperpigmentation. In an embodiment, the formulation is in the form of a serum which must first be shaken, prior to use. For application, a small amount of the serum is placed and smoothed over the affected area of the skin. No rubbing is required.

In one embodiment, the present invention relates to a formulation comprising a therapeutic amount of actives, said actives are selected from the group consisting of caprylic triglycerides, capric triglycerides, hexylresorcinol, ethyl linoleate, tetrapeptide, glycerin, *Rumex occidentalis* extract, ascorbic acid, *Humulus lupulus* extract, and mixtures and combinations thereof.

In another embodiment, the formulation further comprises at least one preservative and the preservative is selected from the group consisting of glyceryl caprylate, glyceryl undecylenate and mixtures and combinations thereof.

In still another embodiment, the formulation further comprises at least one moisturizing agent and the moisturizing agent is selected from the group consisting of glycerin, squalane, and combination and mixtures thereof.

In yet another embodiment, the formulation further comprises at least one serum forming agent and the serum forming agent comprises polyacrylate crosspolymer. In still yet another embodiment, the formulation further comprises at least one penetration enhancer and the penetration enhancer comprises pentylene glycol.

In a further embodiment, the formulation further comprises a hydrating agent, and the hydrating agent is water. In another further embodiment, the formulation further comprises an anti-microbial agent. In yet another further embodiment, the formulation is in the form of a skin lightening serum.

In still another further embodiment, the presently claimed invention relates to a formulation comprising a therapeutic amount of five actives, said five actives consists of: a blend of caprylic or capric triglycerides, hexylresorcinol, and ethyl linoleate; hexylresorcinol; a blend of tetrapeptide and glycerin; a blend of *Rumex occidentalis* extract, ascorbic acid and glycerin; and a blend of *Humulus lupulus* extract, caprylic or capric triglycerides. The ingredients are marketed as the Founding Five or Founding Five Technology™.

In another embodiment, the actives are incorporated into a serum. In a further embodiment, each of the five actives are in the amount from about 0.5 to about 10% by weight of said formulation.

In still a further embodiment, the formulation further comprises a preservative (such as cosphaderm or glyceryl caprylate, glyceryl undecylenate) in the amount from about 0.1 to about 5.0% by weight of said formulation. In yet a further embodiment, the formulation comprises a moisturizing agent (such as glycerin or squalane) in the amount from about 1.0 to about 10.0% by weight of said formulation. In still yet a further embodiment, the formulation further comprises a serum forming agent (such as sepicmac or polyacrylate crosspolymer-6) in the amount from about 0.1 to about 5.0% by weight of said formulation. In another embodiment, the formulation further comprises a penetration enhancer (such as pentylene glycol) in the amount from about 1.0 to about 20.0% by weight of said formulation. In a further embodiment, the formulation further comprises a hydrating agent (water) in the amount from about 10.0 to about 65.0% by weight of said formulation. In another further embodiment, the formulation further comprises a fragrance in the amount from about __ to about __% by weight of said formulation.

In still yet another further embodiment, the formulation further comprises an additive, said additive being selected from the group consisting of a preservative, a moisturizing agent, a serum forming agent, a penetration enhancer, a hydrating agent, a fragrance, a colorant, and mixture and combinations thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

In another embodiment, the Founding Five Technology™ comprises the following:

- Asyntra® SL—A skin lightening, tone-evening synergistic blend that inhibits multiple sites in the melanogenesis pathway. Asyntra® SL is clinically demonstrated to reduce skin hyperpigmentation and comprises Caprylic/Capric Triglyceride (and) Hexylresorcinol (and) Ethyl Linoleate.
- Synovea® HR—This is a safe & effective active skin lightener with skin protective properties. Synovea® HR modulates the melanogenesis pathway and stimulates glutathione. Synovea® HR comprises hexylresorcinol, which is clinically proven to be four-times more effective than Hydroquinone.
- TEGO® Pep 4—Even-Visibly diminishes hyperchromatic spots, alleviates melasma on ethnic skin, brightens the skin, and reduces acne lesions. This ingredient comprises Tetrapeptide-30 and glycerin. Applications for this product include: skin lightening preparations, anti-aging preparations with correction of age spots & pigmentation disorders, anti-aging products for even skin.
- Tyrostat™ 11 is a potent strong inhibitor of tyrosinase enzymatic activity, one of the main enzymes involved in the pigmentation process. It has higher activity than arbutin, turmeric, and hydroquinone, with no unwanted side effects. Tyrostat™ 11 safely reduces skin pigmentation and erythema by limiting both melanin production and skin reddening for an even skin complexion. There are outstanding results after 3 weeks in the reduction of the appearance of age spots. It comprises *Rumex occidentalis* extract, ascorbic acid and glycerin.
- Wonderlight™ decreases hyperpigmentation accentuated by age and stress: lentigines, ephelides, post inflammatory spots and melasma. It interacts with both keratinocytes and melanocytes by blocking signaling pathways involved in the melanin synthesis. Wonderlight™ comprises *Humulus lupulus* (Hops) Extract, and Caprylic/Capric Triglyceride.

Caprylic/Capric Triglycerides

It helps smooth skin. It also binds other ingredients together, and can work as a preservative of sorts to make the active ingredients in cosmetics last longer. Caprylic triglyceride is valued as a more natural alternative to other synthetic chemicals found in topical skin products. Caprylic triglycerides are compounds made of naturally occurring fatty acids. They're a clear liquid and slightly sweet to the taste. The high fat content in triglycerides, along with their texture; make them of particular use for soap and skin care products.

Capric/caprylic triglyceride may function as emollients, dispersing agents, and solvents. As an emollient, caprylic triglyceride is an effective skin-softening ingredient. As a solvent, Caprylic triglyceride can dissolve compounds that are designed to clump together. While some solvents have toxic ingredients, caprylic triglyceride doesn't carry those risks.

Hexylresorcinol

Hexylresorcinol is a substituted dihydroxybenzene. It exhibits antiseptic, anthelmintic, and local anesthetic properties. Hexylresorcinol is a synthetic ingredient that offers several benefits for skin. Its antioxidant benefits include helping to prevent collagen breakdown, preserving skin's firmness. It is capable of scavenging free radicals that damage skin's protein and lipid (fat) components, helping to maintain a healthy appearance. It also plays a role in interrupting specific pathways in skin that lead to hyperpigmentation and uneven skin tone, thus improving the uniformity of skin's surface color.

Ethyl Linoleate

Ethyl linoleate is a long-chain fatty acid ethyl ester resulting from the formal condensation of the carboxy group of linoleic acid with the hydroxy group of ethanol. Ethyl linoleate is a natural product found in Desmos cochinchinensis, Achillea millefolium, and other organisms.

Ethyl Linoleate is reported to accelerate the healing of wounds and clinically proven to be an effective anti-acne agent. It is also reported to correct follicular keratinization, reduce sebum production, lighten skin pigmentation, and provide anti-inflammatory benefits.

Tetrapeptide

A tetrapeptide is a peptide, classified as an oligopeptide, since it only consists of four amino acids joined by peptide bonds. Tetrapeptide-30 is a synthetic peptide containing the amino acids proline, glutamic acid, and lysine. It acts on and within specific targets of skin to reduce factors and interrupt the pathways that lead to the appearance of discolorations and uneven skin tone.

Glycerin

Glycerin, also known as glycerol, is a natural compound derived from vegetable oils or animal fats. It's a clear, colorless, odorless, and syrupy liquid with a sweet taste. Glycerin is a humectant, a type of moisturizing agent that pulls water into the outer layer of your skin from deeper levels of your skin and the air.

In skin care products, glycerin is commonly used with occlusives, another type of moisturizing agent, to trap the moisture it draws into the skin. Glycerin can: hydrate the outer layer of the skin (stratum corneum); improve skin barrier function; provide protection against skin irritants; accelerate wound-healing processes; and relieve dry skin.

*Rumex occidentalis* Extract

*Rumex* Extract is derived from Field Dock—a plant native to Canadian prairies. This botanical extract, native to North America, is effective at reducing unwanted skin coloration, such as sun spots, age spots and freckles. *Rumex occidentalis*, also known as Western Dock, restricts the production of melanin, (the cause of our skin pigmentation), and blocks melanin synthesis. *Rumex* is also used to treat hyperpigmentation by inhibiting the enzyme (tyrosinase) which causes the development of pigmentation in skin. The result is a more even skin tone.

Ascorbic Acid

L-Ascorbic acid or vitamin C is an antioxidant that will help protect the skin to reduce damage caused by sun exposure and other environmental factors that lead to signs of aging. Using vitamin C topically can also assist in the production of collagen to reduce wrinkles and fine lines by restoring elasticity and firmness lost with aging.

The benefits of Vitamin C include, but are not limited to: reducing wrinkles; protecting collagen and increases production; aiding wound healing; helping protect against sun damage; reducing hyperpigmentation; evening skin tone; brightening complexion; and acting like armor against pollution and other free radicals

*Humulus lupulus* Extract

The flower extracts of *Humulus lupulus*, commonly known as hops, contained humulone, lupulone, and xanthohumol, which have shown moderate to strong anticollagenase inhibitory activities and exhibited bactericidal activity. Hops are a great ingredient for minimizing the appearance of pores or fine wrinkles because they contain tannins that can aid to tighten and tone the skin. Overall, hops's antibacterial, anti-inflammatory, antioxidant, hydrating, and astringent characteristics make it a useful cosmetic ingredient.

In one of the embodiments of the present invention, Table 1, set forth below, represents a formulation for treatment of hyperpigmentation including melasma:

TABLE 1

| Active Agents: | % By Weight of Formulation |
|---|---|
| Phase A: | |
| Hydrating agent | from about 10.0 to about 65.0% |
| Polyacrylate crosspolymer-6 | from about 0.1 to about 5.0% |
| Glycerin | from about 1.0 to about 10.0% |
| Phase B: | |
| Squalane | from about 1.0 to about 10.0% |
| Pentylene glycol | from about 1.0 to about 20.0% |
| Blend of caprylic or capric triglycerides, hexylresorcinol, and ethyl linoleate | from about 0.5 to about 10% |
| Hexylresorcinol | from about 0.5 to about 10% |
| Blend of tetrapeptide and glycerin | from about 0.5 to about 10% |
| Blend of rumex occidentalis extract, ascorbic acid and glycerin; | from about 0.5 to about 10% |
| Blend of humulus lupulus extract, caprylic or capric triglycerides | from about 0.5 to about 10% |
| Glyceryl caprylate, glyceryl undecylenate | from about 0.1 to about 5.0% |

The ingredients of Phase A are first admixed in a cold process to create a serum structure. The ingredients of Phase B are then admixed into Phase A until uniform. In another further embodiment, the serum is light yellow and unscented.

In another one of the embodiments of the present invention, Table 2, set forth below, represents another formulation for treatment of hyperpigmentation including melasma:

TABLE 2

| Active Agents: | % By Weight of Formulation |
|---|---|
| Phase A: | |
| Water | from about 10.0 to about 65.0% |
| Serum forming agent | from about 0.1 to about 5.0% |
| Moisturizing agent | from about 1.0 to about 10.0% |
| Phase B: | |
| Squalane | from about 1.0 to about 10.0% |
| Pentylene glycol | from about 1.0 to about 20.0% |
| Blend of caprylic or capric triglycerides, hexylresorcinol, and ethyl linoleate | from about 0.5 to about 10% |
| Hexylresorcinol | from about 0.5 to about 10% |
| Blend of tetrapeptide and glycerin | from about 0.5 to about 10% |
| Blend of rumex occidentalis extract, ascorbic acid and glycerin; | from about 0.5 to about 10% |
| Blend of humulus lupulus extract, caprylic or capric triglycerides | from about 0.5 to about 10% |
| Preservative | from about 0.1 to about 5.0% |

The ingredients of Phase A are first admixed in a cold process to create a serum structure. The ingredients of Phase B are then admixed into Phase A until uniform. In another further embodiment, the serum may be colored or colorless; and may also be scented and unscented.

Among those benefits and improvements that have been disclosed, other objects and advantages of this invention will become apparent from the following description taken in conjunction with the accompanying drawings. The tables and examples constitute a part of this specification and include exemplary embodiments of the present invention and illustrate various objects and features thereof.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A formulation consisting of caprylic triglycerides, capric triglycerides, hexylresorcinol, ethyl linoleate, tetrapeptide, glycerin, *Rumex occidentalis* extract, ascorbic acid, *Humulus lupulus* extract, at least one preservative, at least one moisturizing agent, at least one serum forming agent, at least one penetration enhancer, a hydrating agent, an antimicrobial agent, and a fragrance, said at least one preservative is selected from the group consisting of glyceryl caprylate, glyceryl undecylenate and mixtures and combinations thereof, said at least one moisturizing agent is squalane, said at least one serum forming agent is polyacrylate crosspolymer, said at least one penetration enhancer is pentylene glycol, and said hydrating agent is water.

2. A formulation comprising a therapeutic amount of five actives, said five actives consists of: a blend of caprylic or capric triglycerides, hexylresorcinol, and ethyl linoleate; hexylresorcinol; a blend of tetrapeptide and glycerin; a blend of *Rumex occidentalis* extract, ascorbic acid and glycerin; and a blend of *Humulus lupulus* extract, caprylic or capric triglycerides.

3. The formulation of claim 2 wherein said actives are incorporated into a serum.

4. The formulation of claim 2 wherein each of the five actives are in the amount from about 0.5 to about 10% by weight of said formulation.

5. The formulation of claim 2 further comprises a preservative in the amount from about 0.1 to about 5.0% by weight of said formulation.

6. The formulation of claim 2 further comprises a moisturizing agent in the amount from about 1.0 to about 10.0% by weight of said formulation.

7. The formulation of claim 2 further comprises a serum forming agent in the amount from about 0.1 to about 5.0% by weight of said formulation.

8. The formulation of claim 2 further comprises a penetration enhancer in the amount from about 1.0 to about 20.0% by weight of said formulation.

9. The formulation of claim 2 further comprises a hydrating agent in the amount from about 10.0 to about 65.0% by weight of said formulation.

10. The formulation of claim 2 further comprises an additive, said additive being selected from the group consisting of a preservative, a moisturizing agent, a serum forming agent, a penetration enhancer, a hydrating agent, a fragrance, a colorant, and mixture and combinations thereof.

* * * * *